US010898383B2

(12) United States Patent
Barker et al.

(10) Patent No.: US 10,898,383 B2
(45) Date of Patent: Jan. 26, 2021

(54) SYSTEMS AND METHODS FOR TISSUE DISSECTION IN CORNEAL TRANSPLANTS

(71) Applicant: SightLife Surgical, Winston-Salem, NC (US)

(72) Inventors: Jerry W. Barker, Gretna, VA (US); Douglas C. Drabble, Winston-Salem, NC (US); Peter R. Andrews, Boulder, CO (US)

(73) Assignee: CORNEAGEN, INC., Seattle, WA (US)

( * ) Notice: Subject to any disclaimer, the term of this patent is extended or adjusted under 35 U.S.C. 154(b) by 223 days.

(21) Appl. No.: 16/054,066

(22) Filed: Aug. 3, 2018

(65) Prior Publication Data

US 2019/0038465 A1    Feb. 7, 2019

Related U.S. Application Data

(60) Provisional application No. 62/541,233, filed on Aug. 4, 2017.

(51) Int. Cl.
*A61F 9/013* (2006.01)
*A61F 2/14* (2006.01)

(52) U.S. Cl.
CPC ............ *A61F 9/0133* (2013.01); *A61F 2/142* (2013.01); *A61F 2/148* (2013.01); *A61F 2240/001* (2013.01)

(58) Field of Classification Search
CPC .... A61F 2240/001; A61F 2/142; A61F 2/148; A61F 9/0133; A61B 2017/320024; A61B 17/00234; A61B 17/32002; A61B 17/3423; A61B 2017/320775; A61B 17/320016

See application file for complete search history.

(56) References Cited

U.S. PATENT DOCUMENTS

| 4,423,728 A | 1/1984 | Lieberman |
| 4,429,696 A | 2/1984 | Hanna |
| 5,269,795 A * | 12/1993 | Arnott ................. A61F 9/00802 606/166 |
| 5,755,785 A | 5/1998 | Rowsey et al. |

(Continued)

OTHER PUBLICATIONS

International Search Report for PCT/US2018/045169, dated Oct. 24, 2018.

*Primary Examiner* — George J Ulsh
*Assistant Examiner* — Andrew P. Restaino
(74) *Attorney, Agent, or Firm* — Polsinelli PC; Michelle L. McMullen; J. Wendy Davis

(57) ABSTRACT

A dissection system for corneal transplants includes a housing including a contact side to be positioned against a cornea. The housing includes an interior passageway with an opening at the contact side. The dissection system includes a blade assembly disposed in the interior passageway. The blade assembly includes a first blade and a second blade. The first blade includes a first cutting edge and the second blade includes a second cutting edge. The first blade and the second blade are movable relative to the housing such that the first cutting edge and the second cutting edge extend through the opening of the housing and out of the interior passageway. The first cutting edge produces a first cut in the cornea. The second cutting edge produces a second cut in the cornea. The first cut and the second cut define a volume of tissue for removal from the cornea.

27 Claims, 9 Drawing Sheets

(56) References Cited

U.S. PATENT DOCUMENTS

| | | |
|---|---|---|
| 6,613,061 B1 | 9/2003 | Olson et al. |
| 7,744,614 B2 | 6/2010 | Gayheart et al. |
| 7,753,927 B2 | 7/2010 | Weston |
| 2009/0069817 A1 | 3/2009 | Peyman |
| 2017/0189234 A1 | 7/2017 | Thistle |
| 2019/0380868 A1* | 12/2019 | Jacob ..................... A61F 9/007 |

* cited by examiner

SYSTEMS AND METHODS FOR TISSUE DISSECTION IN CORNEAL TRANSPLANTS

CROSS-REFERENCE TO RELATED APPLICATIONS

This application claims the benefit of, and priority to, U.S. Provisional Patent Application Ser. No. 62/541,233, filed Aug. 4, 2017, the contents of which are incorporated entirely herein by reference.

BACKGROUND

Field

The present disclosure pertains to systems and methods for transplanting a cornea to treat disorders of the eye, and more particularly, to systems and methods for dissecting tissue for corneal transplants.

Description of Related Art

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor.

SUMMARY

Systems and methods of the present disclosure employ a manual dissection system to remove diseased/damaged tissue from a cornea according to dimensions that match a corneal implant. For instance, to minimize the removal of the endothelium in a full-thickness transplant, the manual dissection system may remove a volume of diseased/damaged tissue according to a mushroom shape.

According to an example embodiment, a dissection system for corneal transplants includes a housing including a contact side configured to be positioned against a cornea. The housing includes an interior passageway with an opening at the contact side. The dissection system includes a blade assembly disposed in the interior passageway of the housing. The blade assembly includes a first blade and a second blade. The first blade includes a first cutting edge and the second blade includes a second cutting edge. The first blade and the second blade are movable relative to the housing such that the first cutting edge and the second cutting edge extend through the opening of the housing and out of the interior passageway. The first cutting edge is configured to produce a first cut in the cornea disposed at the contact side and the second cutting edge is configured to produce a second cut in the cornea. The first cut and the second cut defines a volume of tissue for removal from the cornea. The dissection system includes one or more manipulators configured to move the first blade and the second blade relative to the housing. The system may further include one or more cutting mechanisms configured to make further cuts transverse to at least one of the first cut or the second cut. The one or more cutting mechanisms may include one or more wires, and the one or more manipulators may be configured to move the wires to make the transverse cuts.

According to another example embodiment, a method operates a dissection system for corneal transplants. The dissection system includes a housing including a contact side configured to be positioned against a cornea, the housing including an interior passageway with an opening at the contact side. The dissection system includes a blade assembly disposed in the interior passageway of the housing. The blade assembly includes a first blade and a second blade, the first blade including a first cutting edge, the second blade including a second cutting edge, and the first blade and the second blade being movable relative to the housing. The dissection system includes one or more manipulators. The method includes positioning the contact side of the housing against a cornea. The method includes operating the one or more manipulators to move the first blade and the second blade relative to the housing such that the first cutting edge and the second cutting edge extend past the opening of the housing and out of the interior passageway. The first cutting edge produces a first cut in the cornea disposed at the contact side and the second cutting edge produces a second cut in the cornea, the first cut and the second cut defining a volume of tissue for removal from the cornea. The method may further include making further cuts, with one or more cutting mechanisms, transverse to at least one of the first cut or the second cut. The one or more cutting mechanisms may include one or more wires, and the method may further comprise operating the one or more manipulators to move the wires to make the transverse cuts.

DETAILED DESCRIPTION

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor.

From the outer (anterior) surface of the eye to the inner (posterior) parts, the structure of the cornea includes five layers: (1) epithelium, (2) Bowman's layer, (3) stroma, (4) Descemet's membrane, and (5) endothelium. Penetrating keratoplasty (PK) involves a full-thickness transplant where all layers of the cornea from the epithelium to the endothelium are removed and replaced with a corneal implant. In PK, a manual dissection device known as a trephine may be employed to remove the full thickness of existing corneal tissue. The trephine may also be used to cut a donor cornea to provide the corneal implant that dimensionally matches the removed corneal tissue. The corneal implant is then positioned in place of the removed corneal tissue and sutured into place.

Anterior lamellar keratoplasty (ALK) is an alternative treatment that selectively replaces diseased/damaged tissue in an anterior part of the cornea. A type of ALK procedure is deep anterior lamellar keratoplasty (DALK) which removes the epithelium, Bowman's layer, and the stroma but leaves the native Descemet's membrane and endothelium in place. In ALK, the surgeon dissects the cornea and removes the anterior part of the cornea. A dimensionally matching corneal implant from a donor cornea is then positioned in a bed formed by the removal of corneal tissue and sutured into place.

ALK is less invasive than PK and is preferred when the endothelium is healthy. In contrast to the cells of the epithelium and the stroma, the cells of the endothelium cannot regenerate. With ALK, patients retain their own endothelium so the risk of rejection by the immune system may be dramatically reduced.

Figure 1:
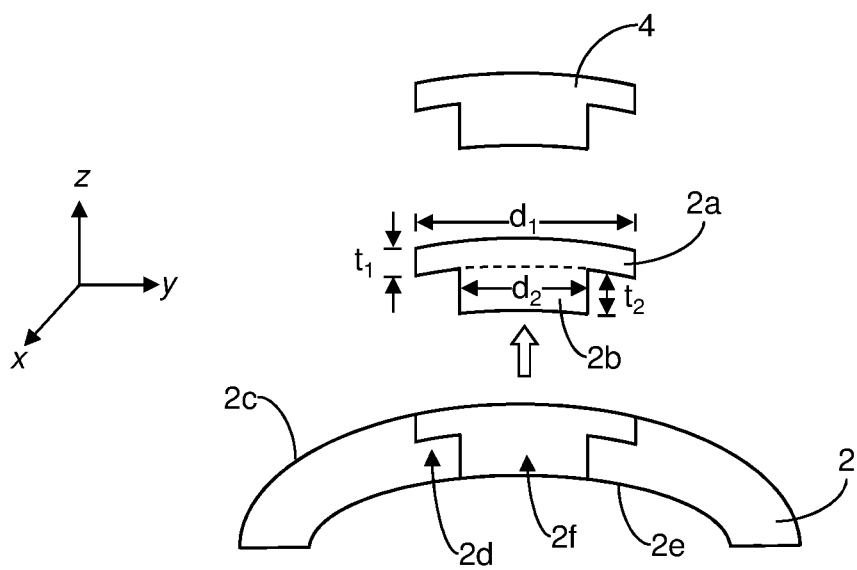
FIG. 1 illustrates example removal of tissue from a cornea according to a mushroom shape and a correspondingly shaped corneal implant received by a bed in the cornea formed by the removal of the tissue.

Although PK involves a full-thickness transplant, certain approaches for PK attempt to minimize the removal of the endothelium. For instance, a patient may have a healthy endothelium, but central corneal scars and full-thickness opacities require a full-thickness transplant. As shown in FIG. 1, an example approach for PK removes an anterior portion $2a$ and a posterior portion $2b$ of tissue from a cornea $2$. The approach illustrated in FIG. 1 can provide more effective and faster healing. The anterior portion $2a$ extends from the epithelial surface $2c$ of the cornea $2$ to a depth in the stroma $2d$ to define a first thickness $t_1$ (along the z-axis as shown). The anterior portion $2a$ has a substantially circular profile along the x-y plane with a first diameter $d_1$. For instance, the first thickness $t_1$ may be approximately 175 μm to approximately 200 μm and the first diameter $d_1$ may be approximately 9 mm. The posterior portion $2b$ extends from the anterior portion $2a$ through the endothelium $2e$ to define a second thickness $t_2$ (along the z-axis). $t_1+t_2$ is the thickness from the epithelial surface $2c$ through the endothelium. The posterior portion $2b$ has a substantially circular profile along the x-y plane with a second diameter $d_2$. For instance, the second thickness $t_2$ may be approximately 350 μm and the second diameter $d_2$ may be approximately 6.5 mm (or larger). The first diameter $d_1$ of the anterior portion $2a$ is greater than the second diameter $d_2$ of the posterior portion $2b$. The difference between the first diameter $d_1$ and the second diameter $d_2$ may be approximately 0.5 mm to approximately 1 mm. As such, the portions $2a, b$ together define a volume of tissue having a mushroom shape. The removal of the posterior portion $2b$ results in the removal of a smaller section of the endothelium than would be the case if the posterior portion $2b$ were to have the same diameter $d_1$ as the anterior portion $2a$ (corresponding to a removal of corneal tissue having a uniform diameter $d_1$).

As also shown in FIG. 1, the removal of the portions $2a, b$ forms a bed $2f$ in the cornea $10$. The bed $2f$ also has a mushroom shape. A corneal implant $4$ is correspondingly shaped to be received in the bed $2f$. Using a microkeratome or other conventional dissection device to manually remove the portions $2a, b$ may not provide the sufficient precision to ensure a dimensional match between the corneal implant $4$ and the bed $2f$. Indeed, the mushroom shape of the corneal implant $4$ and the bed $2f$ makes it a greater challenge to achieve a match. Although a femtosecond laser may be employed to cut the portions $2a, b$ precisely from the cornea $2$, practitioners might not be conveniently equipped with a femtosecond laser system to cut the cornea $2$ according to matching dimensions.

Advantageously, aspects of the present disclosure provide approaches for manually removing corneal tissue with the precision and consistency necessary to match the dimensions of a corneal implant. Such approaches employ devices that are more convenient and cost-effective than a femtosecond laser. With such devices, it is feasible for suppliers to shape a corneal implant with a femtosecond laser or similar high-precision cutting system and for practitioners to remove a volume of tissue manually and form a bed that accurately matches the shape of the corneal implant provided by the supplier.

Figure 2A:
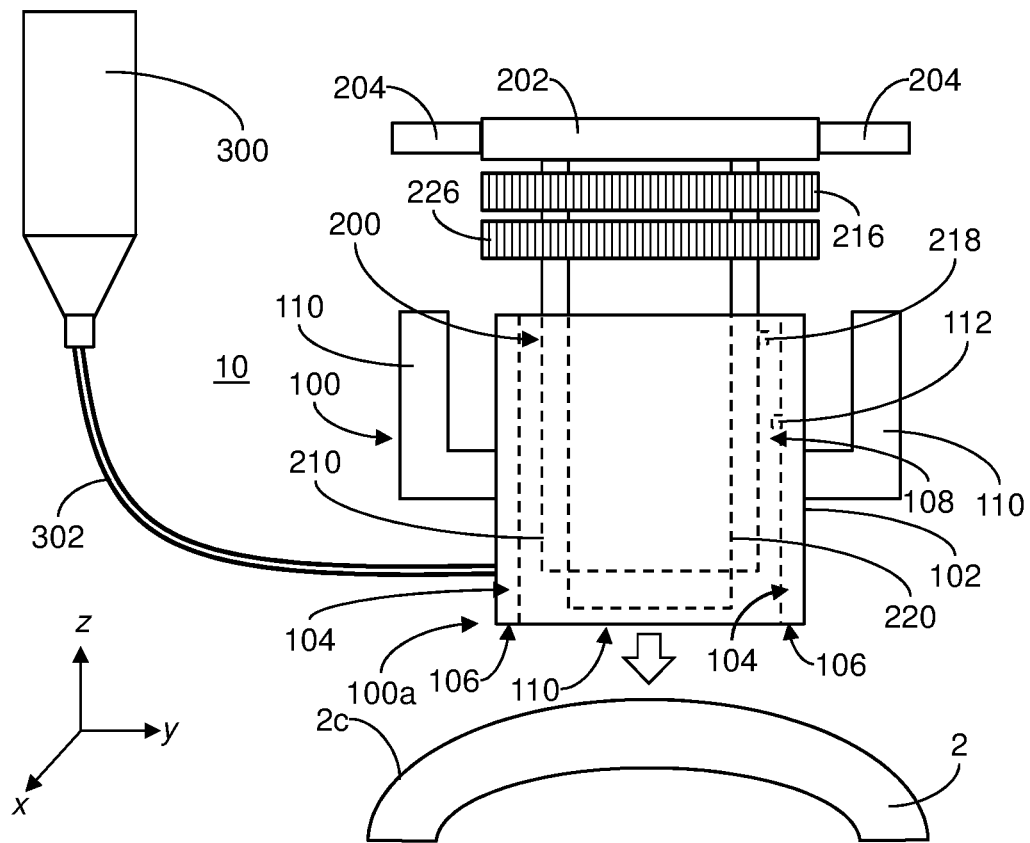
FIG. 2A illustrates an example dissection system for precise manual removal of corneal tissue in a corneal implant, according to aspects of the present disclosure.
Figure 2B:
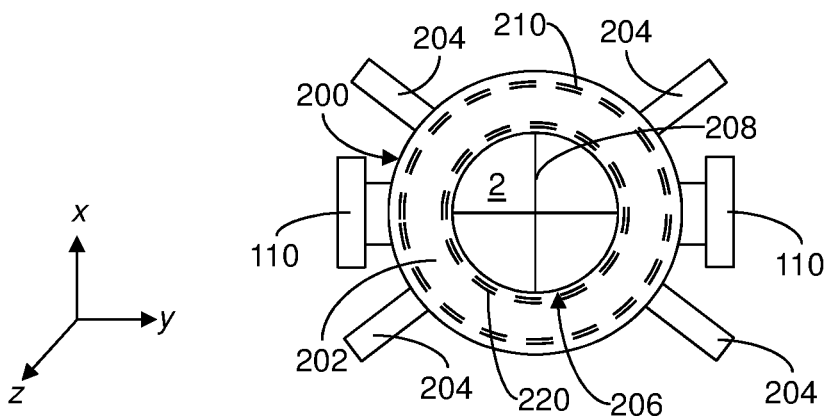
FIG. 2B illustrates a top view of the example dissection system of FIG. 2A.

FIGS. 2A-D illustrate an example dissection system $10$ for manually removing corneal tissue. As shown in FIG. 2A, the dissection system $10$ includes a housing $100$, a blade assembly $200$, and a syringe $300$. The housing $100$ has a contact side $100a$ that can be placed against the cornea $2$. The contact side $100a$ may be contoured to accommodate the general anterior shape of the cornea $2$. The housing $100$ includes a substantially cylindrical outer wall $102$ that extends upwardly from the contact side $100a$ (in the positive-z direction). The housing $100$ includes an interior passageway $108$ with an opening $110$ at the contact side $100a$.

The housing $100$ includes one or more vacuum chambers $104$ that can be coupled to the syringe $300$ or other negative pressure source via a tube $302$. (The vacuum chambers $104$ are selectively shown in FIG. 2A with dashed lines.) The plunger of the syringe $300$ may be drawn back or otherwise operated to provide a negative pressure in the vacuum chambers $104$ via the tube $302$. One or more vacuum openings $106$ for the vacuum chambers $104$ are arranged along the periphery of the opening $110$ at the contact side $100a$. The vacuum openings $106$ can engage the epithelial surface $2c$ of the cornea $10$. Negative pressure in the vacuum chambers $104$ generates suction between the epithelial surface 2c and the housing 100 at the vacuum openings 106, thereby securely fixing the housing 100 to the cornea 2. To decouple the housing 100 from the cornea 2, the syringe 300 can be operated in an opposite manner to create positive pressure in the vacuum chambers 104 and release the suction at the vacuum openings 106.

The housing 100 includes positioning elements 110 that extend radially outward from the outer wall 102. The positioning elements 110 provide sufficient surface area that the practitioner can use to hold and position the housing 100, e.g., between his/her fingers.

The blade assembly 200 is disposed in the interior passageway 108 of the housing 100. The blade assembly 200 includes a manipulator 202, which can be operated to cut the cornea 2 with the blade assembly 200. For instance, a threaded coupling may be provided between the housing 100 and the blade assembly 200. The manipulator 202 may be rotated about the z-axis to cause rotation of the blade assembly 200 relative to the housing 100. As it rotates, the blade assembly 200 also rides along the thread of the coupling, which thus causes the blade assembly 200 to move axially (along the z-axis) relative to the housing 100 and the cornea 2. As shown in the top view of FIG. 2B, the manipulator 202 includes a plurality of radially extending rods 204 which the practitioner can use to rotate the manipulator 202, e.g., with his/her fingers. The practitioner may simultaneously use the positioning elements 110 to hold the housing 100 stably in position while rotating the manipulator 202.

Accordingly, the manipulator 202 can move the blade assembly 200 in the negative-z direction and through the passageway opening 110 until the blade assembly 200 penetrates the cornea 2 positioned against the contact side 100a of the housing 100. The housing 100 is securely coupled to the cornea 2 so that the blade assembly 200 is restricted to predictable and precise movement along the z-axis into the cornea 2.

The blade assembly 200 includes an outer blade 210 and an inner blade 220. (The outer blade 210 and the inner blade 220 are selectively shown in FIGS. 2A, C with dashed lines.) As shown in the partial view of the dissection system 10 in FIG. 2C, the outer blade 210 and the inner blade 220 are substantially tubular. The outer blade 210 includes a central passageway 212 with a substantially circular cutting edge 214. The inner blade 220 is disposed in the central passageway 212 of the outer blade 210 and extends past the cutting edge 214 of the outer blade 210. The inner blade 220 also includes a central passageway 222 with a substantially circular cutting edge 224.

The outer cutting edge 214 and the inner cutting edge 224 are substantially concentric. Correspondingly, the outer blade 210 and the inner blade 220 create substantially concentric circular cuts into the cornea 2. When the blade assembly 200 penetrates the cornea 10, the circular cut made by the outer cutting edge 214 has a larger diameter than the circular cut made by the inner cutting edge 224. For instance, as shown in FIG. 2D, the outer cutting edge 214 may have a diameter that makes a substantially circular outer cut with the first diameter $d_1$, which corresponds to the anterior portion 2a removed from the cornea 2. Additionally, the inner cutting edge 224 may have a diameter that makes a substantially circular inner cut with the second diameter $d_2$, which corresponds to the posterior portion 2b removed from the cornea 2.

The manipulator 202 moves the outer blade 210 and the inner blade 220 simultaneously. As shown in the top view FIG. 2B, the manipulator 202 includes an aperture 206 that aligns with the central passageway 222 of the inner blade 220. As such, the cornea 2 can be seen through the aperture 206 and the central passageway 222. Cross-hairs 208 or other positioning guides may be disposed in the aperture 206 and/or the central passageway 222 to mark the center of the outer blade 210 and the inner blade 220. The practitioner may employ the cross-hairs 208 to fix the housing 100 to the cornea 2 and center the blades 210, 220 over a desired location, e.g., the center, of the cornea 2. As such, the location of the cuts made by the outer cutting edge 214 and the inner cutting edge 224 can be controlled.

Figure 2C:
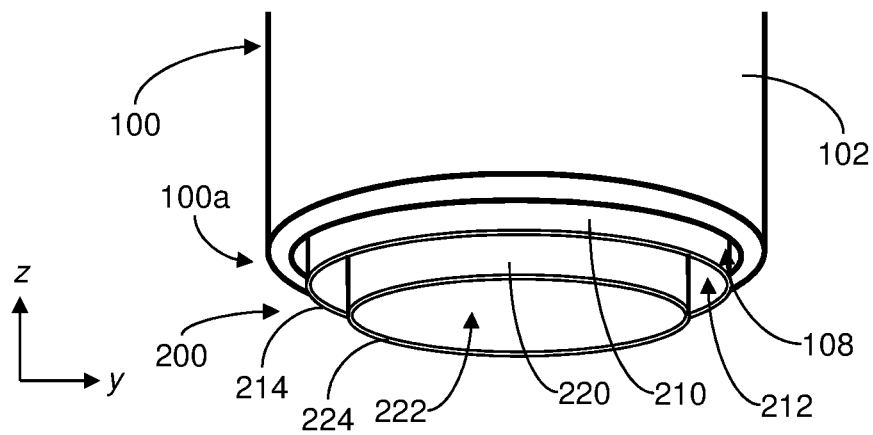
FIG. 2C illustrates a partial perspective view of the example dissection system of FIG. 2A.
Figure 2D:
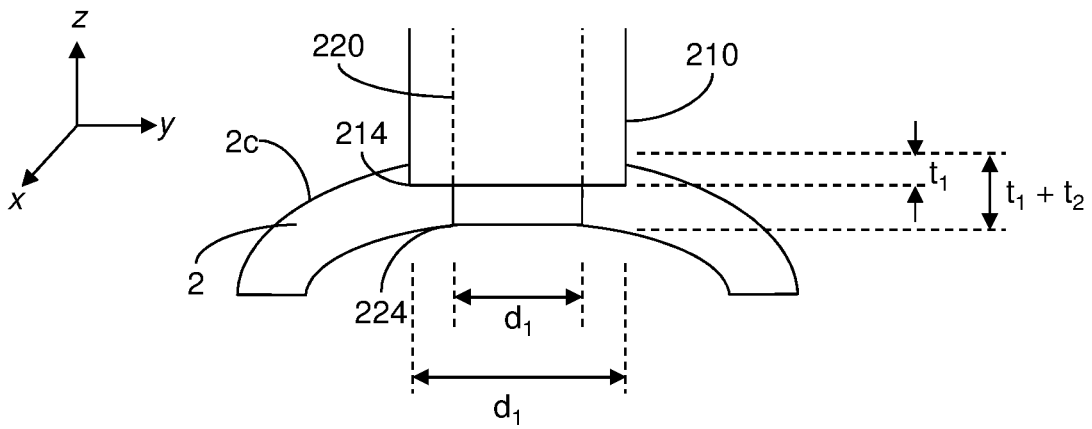
FIG. 2D illustrates an example implementation of the example dissection system of FIG. 2A.

As shown in FIG. 2C, the inner blade 220 extends farther downward in the negative-z direction than the outer blade 210. Thus, when the blade assembly 200 penetrates the cornea 10, the inner blade 220 penetrates the cornea 10 to a greater depth than the outer blade 210. The blade assembly 200 includes an outer blade depth controller 216 to control the penetration depth of the outer blade 210 and an inner blade depth controller 226 to control the penetration depth of the inner blade 220. For instance, the outer blade depth controller 216 and the inner blade depth controller 226 may be separately rotated about the z-axis as manual dials to set the respective penetration depths.

As shown in FIG. 2D, the outer blade depth controller 216 may be operated so that the outer blade 210 moves past the contact side 100a of the housing 100 by a distance that makes an outer cut in the cornea 2 with a depth of $t_1$. This provides the first thickness $t_1$ of the anterior portion 2a. Additionally, the inner blade depth controller 226 may be operated so that the inner blade 220 moves past the contact side 100a of the housing 100 by a distance that makes an inner cut in the cornea 2 with a depth of $t_1+t_2$. This provides the second thickness $t_2$ of the posterior portion 2b.

According to an example embodiment, the outer blade depth controller 216 can move one or more adjustable stops 112 to a position along the interior passageway 108 of the housing 100. One or more corresponding stops 218 are coupled to the outer blade 210. (The stops 112, 218 are selectively illustrated by dashed lines in FIG. 2A.) Thus, when the manipulator 202 is operated, the outer blade 210 can move downwardly in the negative-z direction and penetrate the cornea 2 until the stops 218 of the outer blade 210 reach the stops 112 at the set position. The outer blade depth controller 216 may provide numerical markers to allow the practitioner to dial a position for the stops 112 corresponding to the desired penetration depth $t_1$ for the outer blade 210.

Meanwhile, the inner blade depth controller 226 can adjust the distance between the inner cutting edge 224 and the outer cutting edge 214. For instance, the inner blade 220 may be adjustably coupled to the outer blade 210, e.g., by a threaded coupling, and the inner blade depth controller 226 may be operated to adjust the coupling and set the distance. The inner blade depth controller 226 may provide numerical markers to allow the practitioner to dial the desired thickness $t_2$ for the posterior portion 2b. This thickness is equivalent to the distance between the cutting edges 214, 224.

Once the distance between the cutting edges 214, 224 is set with the inner blade depth controller 226, the manipulator 202 may be operated to move the outer blade 210 as described above. Correspondingly, the inner blade 220 moves with the outer blade 210 at the set distance. As illustrated in FIG. 2D, when the outer blade 210 is stopped from further movement by the stops 112, the outer cutting edge 214 stops its cut at the desired penetration depth $t_1$ and the inner cutting edge 224 stops its cut at the set distance $t_2$ from the outer cutting edge 214. Accordingly, the outer blade 210 creates an outer cut with the depth and diameter to remove the anterior portion 2a, and the inner blade 220 creates an inner cut with the depth and smaller diameter to remove the posterior portion 2b. (The inner cut of the inner blade 220 also passes through the anterior portion 2a but does not affect the outer cut of the outer blade 210.)

After making the desired outer and inner cuts, the housing 100 and the blade assembly 200 can be released from the cornea 2 by operation of the manipulator 202 and the syringe 300. With the precise outer and inner cuts, a separate dissection device or other manual instrument may be employed to remove the anterior portion 2a and the posterior portion 2b. In particular, to remove the anterior portion 2a, an annular cut is made at substantially the penetration depth of $t_1$ for the outer blade, between the outer cut to the inner cut. Additionally, to remove the posterior portion 2b, a circular cut defined by the circumference of the inner cut is made at substantially the penetration depth of $t_1+t_2$ for the inner blade. As described above, the removal of the portions 2a, b produces a bed 2f for receiving the corneal implant 4. With the precision of the cuts by the dissection system 10, the bed 2f provides a dimensional match with the corneal implant 4.

Figure 3:
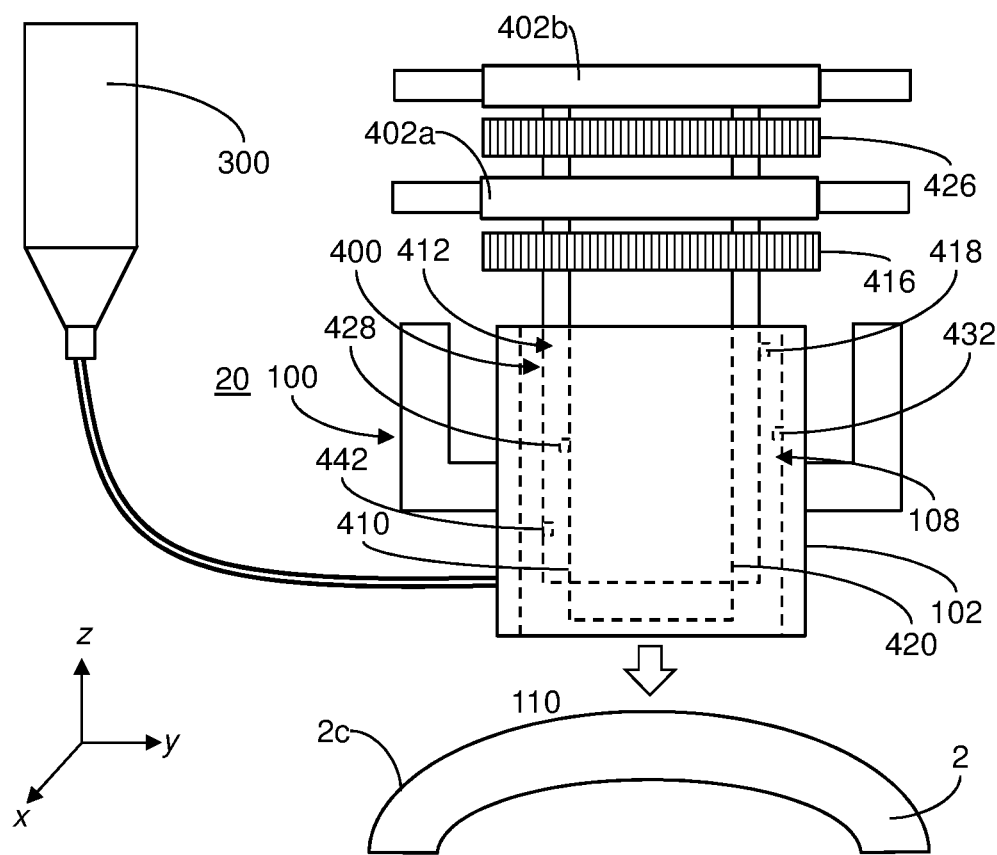
FIG. 3 illustrates another example dissection system for precise manual removal of corneal tissue in a corneal implant, according to aspects of the present disclosure.

Aspects of the present disclosure are not limited to the embodiment described in FIGS. 2A-D. For instance, FIG. 3 illustrates another example dissection system 20 including an alternative blade assembly 400 with an outer blade 410 and an inner blade 420. In contrast to the outer blade 210 and the inner blade 220 described above, the movement of the inner blade 420 is not coupled to the movement of the outer blade 410. As such, the blade assembly 400 includes a first manipulator 402a to move the outer blade 410 along the z-axis and a second manipulator 402b to move the inner blade 420 separately along the z-axis.

The blade assembly 400 includes an outer blade depth controller 416 that can move one or more adjustable stops 432 to a position along the interior passageway 108 of the housing 100. One or more corresponding stops 418 are coupled to the outer blade 410. Similar to the manipulator 202, when the manipulator 402a is operated, the outer blade 410 can move downward in the negative-z direction and penetrate the cornea 2 until the stops 418 of the outer blade 410 reach the stops 432 at the set position. The outer blade depth controller 416 may provide numerical markers to allow the practitioner to dial a position for the stops 432 corresponding to the desired penetration depth $t_1$ for the outer blade 410.

The operation of the manipulator 402a, however, does not move the inner blade 420. Thus, the blade assembly 400 includes an inner blade depth controller 426 that that can move one or more adjustable stops 442 to a position along a central passageway 412 of the outer blade 410. One or more corresponding stops 428 are coupled to the inner blade 420. When the manipulator 402b is operated, the inner blade 420 can move in the negative-z direction and penetrate the cornea 2 until the stops 428 of the inner blade 420 reach the stops 442 at the set position. The inner blade depth controller 426 may provide numerical markers to allow the practitioner to dial a position for the stops 442 corresponding to the desired penetration depth $t_1+t_2$ for the inner blade 420. Accordingly, the practitioner operates each of the manipulators 402a, b separately to make the respective outer and inner cuts.

Figure 4:
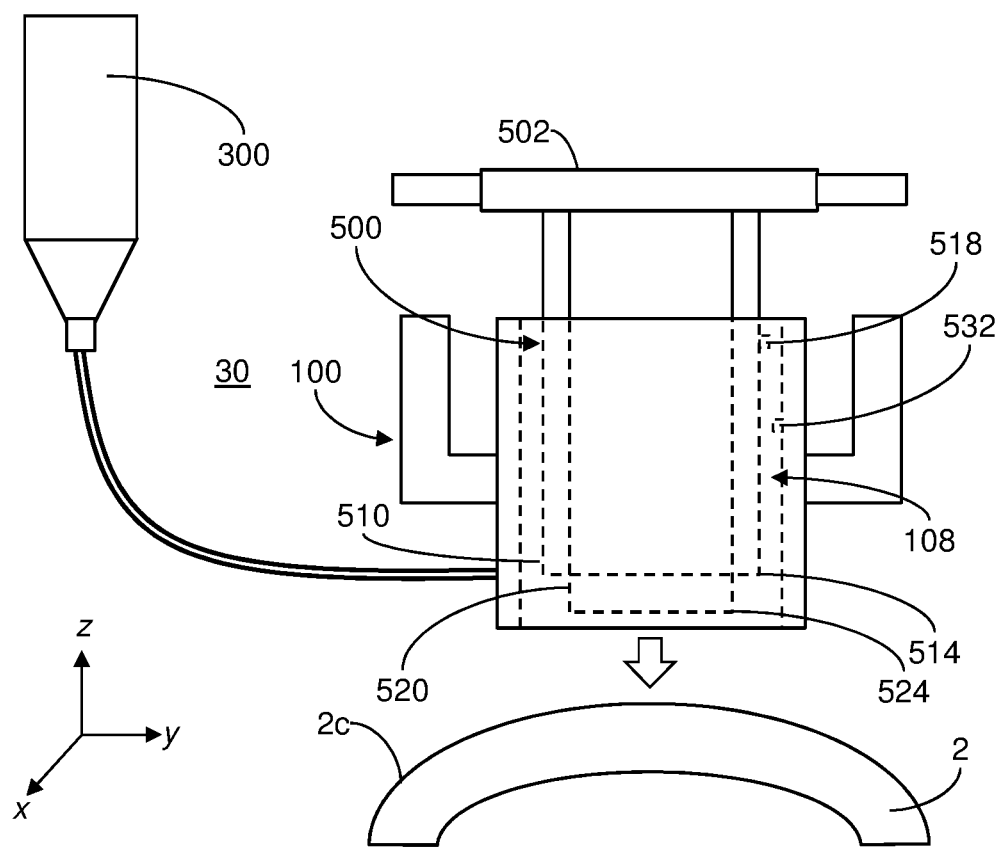
FIG. 4 illustrates yet another example dissection system for precise manual removal of corneal tissue in a corneal implant, according to aspects of the present disclosure.

FIG. 4 illustrates another example dissection system 30 including an alternative blade assembly 500 as well as the housing 100 and the syringe 300. In contrast to the blade assemblies 200, 400 described above, the blade assembly 500 includes an outer blade 510 and an inner blade 520 with constant respective penetration depths. In other words, blade assembly 500 does not employ depth controllers that allow the respective penetration depths to be adjusted. For instance, one or more stops 532 are fixedly positioned along the interior passageway 108 of the housing 100. One or more corresponding stops 518 are coupled to the outer blade 510. The blade assembly 500 includes a manipulator 502 that can be operated to move the outer blade 510 in the negative-z direction and penetrate the cornea 2 until the stops 518 of the outer blade 510 reach the stops 532 at the set position. The position for the stops 532 corresponds to the desired penetration depth $t_1$ for the outer blade 510.

Additionally, the position of the inner blade 520 relative to the outer blade 510 cannot be adjusted. The inner blade 520 has an inner cutting edge 524 that is fixedly positioned at a distance $t_2$ from an outer cutting edge 514 of the outer blade 510. As such, when the outer blade 510 reaches the desired penetration depth $t_1$, the inner blade 520 reaches a desired penetration depth $t_1+t_2$. Accordingly, the practitioner operates the manipulator 502 to make the same outer and inner cuts.

As described above, a separate dissection device or other manual instrument may be employed to remove the anterior portion 2a and the posterior portion 2b after a blade assembly 200, 400, 500 has been manipulated to make cuts in the cornea with the outer blade and the inner blade. In alternative embodiments, however, the blade assembly may be configured to make further cuts to remove the anterior portion 2a and the posterior portion 2b. Such a blade assembly eliminates the need for a separate dissection device or other manual instrument. In particular, to remove the anterior portion 2a, the blade assembly can make a cut (e.g., an annular cut) at the penetration depth of $t_1$, between the outer cut to the inner cut. Additionally, to remove the posterior portion 2b, the blade assembly can make a cut (e.g., a circular cut) defined by the inner cut at the penetration depth of $t_1+t_2$. The annular and circular cuts are generally transverse to the outer and inner cuts, respectively.

Figure 5A:
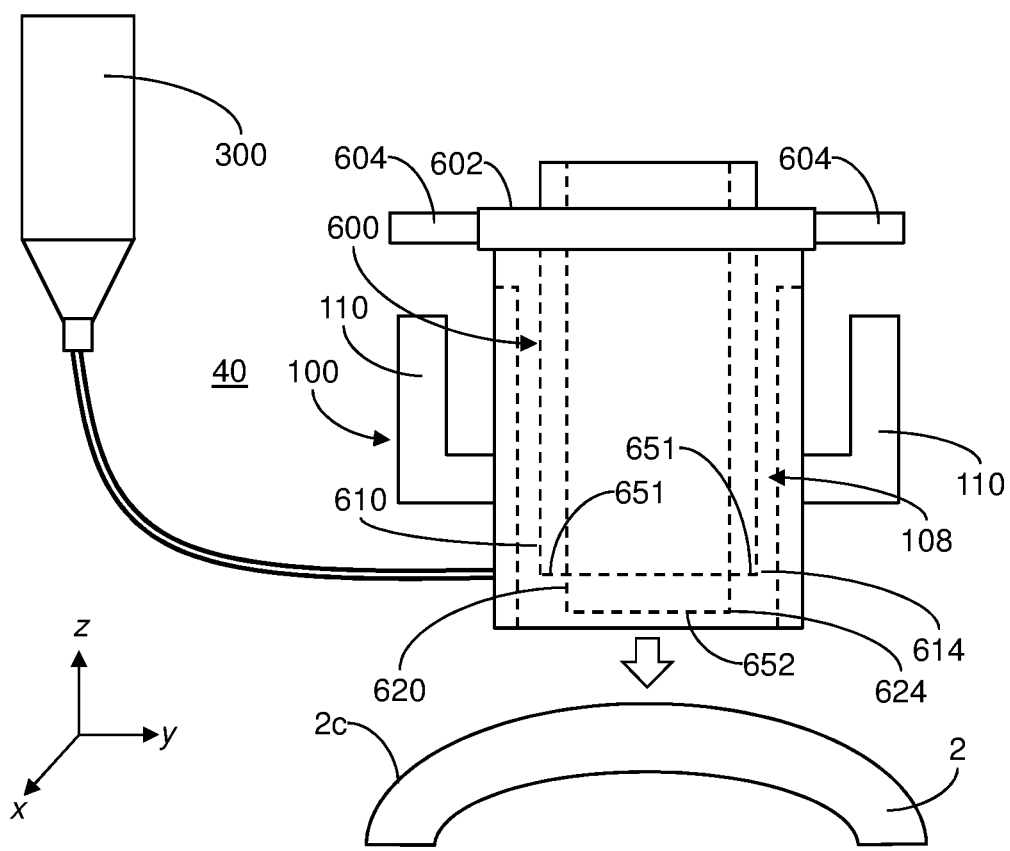
FIG. 5A illustrates a further example dissection system for precise manual removal of corneal tissue in a corneal implant, including an additional cutting mechanism for making cuts after penetration of outer/inner blades into the cornea, according to aspects of the present disclosure.
Figure 5B:
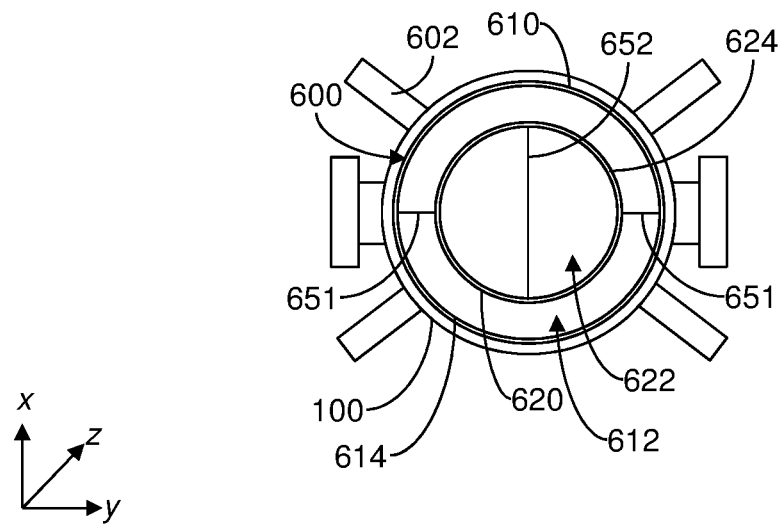
FIG. 5B illustrates a bottom view of the example dissection system of FIG. 5A.
Figure 5C:
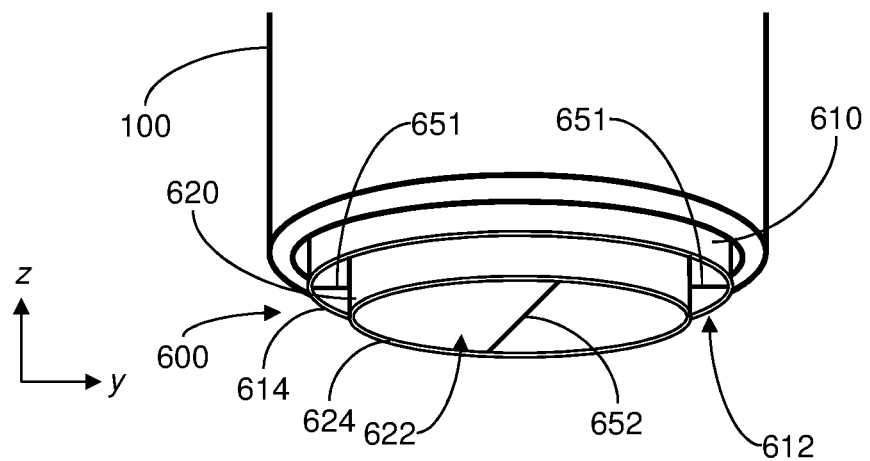
FIG. 5C illustrates a partial perspective view of the example dissection system of FIG. 5A.

FIGS. 5A-C illustrate an example dissection system 40 employing a blade assembly 600. Like the blade assembly 500 described above, the blade assembly 600 includes an outer blade 610 and an inner blade 620 with constant respective penetration depths. The inner blade 620 has an inner cutting edge 624 that is fixedly positioned at a distance $t_2$ from an outer cutting edge 614 of the outer blade 610. As such, when the outer blade 610 reaches the desired penetration depth $t_1$, the inner blade 620 reaches a desired penetration depth $t_1+t_2$.

The dissection system 40 includes the housing 100 and the syringe 300. As described above, the housing 100 can be positioned securely against the cornea 2 with the use of a negative pressure provided by the syringe 300. The blade assembly 600 is disposed in the interior passageway 108 of the housing 100. The housing 100 thus positions the blade assembly 600 relative to the cornea 2.

The blade assembly 600 includes a manipulator 602 that can be rotated about the z-axis to cause the outer blade 610 to move relative to the housing 100 and the cornea 2. Such movement of the outer blade 610 results in corresponding movement of the inner blade 620, which is fixed relative to the outer blade 610. The manipulator 602 can be rotated to cause penetration of the outer blade 610 to a desired depth $t_1$ and penetration of the inner blade 620 to a desired depth $t_1+t_2$. The manipulator 602 includes a plurality of radially extending rods 604 which the practitioner can use to rotate the manipulator 602, e.g., with his/her fingers. The practitioner may simultaneously use the positioning elements 110 to hold the housing 100 stably in position while rotating the manipulator 602.

The blade assembly 600 can make an annular cut at the penetration depth $t_1$ between the cuts made by the outer blade 610 and the inner blade 620. Additionally, at the penetration depth $t_1+t_2$, the blade assembly 600 can make a circular cut with a circumference defined by the inner blade 620. Together, the annular cut and the circular cut allow the anterior portion 2a and the posterior portion 2b to be removed.

As shown in FIGS. 5B-C, the blade assembly 600 includes wires 651 (or similar cutting structures) that extend between the outer blade 610 and the inner blade 620 within the central passageway 612 of the outer blade 610. The wires 651 are aligned with the outer cutting edge 614 of the outer blade 610 (i.e., generally, at the same position on the z-axis as the outer cutting edge 614). Additionally, the blade assembly 600 includes a wire 652 (or similar cutting structure) that extends across the central passageway 222 of the inner blade 620. The wire 652 is aligned with the inner cutting edge 612 of the inner blade 610 (i.e., generally, at the same position on the z-axis as the inner cutting edge 612).

When the outer cutting edge 614 of the outer blade 610 penetrates the cornea 2 to the desired depth $t_1$, the wires 651 also penetrate the cornea 2 to the desired depth $t_1$. Meanwhile, when the inner cutting edge 624 of the inner blade 620 correspondingly penetrates the cornea 2 to the desired depth $t_1+t_2$, the wire 652 also penetrates the cornea to the desired depth $t_1+t_2$. The wires 651, 652 have sufficient tension and sharpness to cut through the cornea 2 and do not generate significant resistance against the movement of the outer blade 610 and the inner blade 610. Although FIGS. 5B-C illustrate two wires 651 and one wire 652 as an example, embodiments may employ different numbers of wires 651 and/or wires 652. The wires 651, 652 can penetrate the cornea 2, because the outer blade 610 and the inner blade 620 do not rotate relative to the housing 100 and the cornea 2 when penetrating the cornea 2.

Figure 5D:
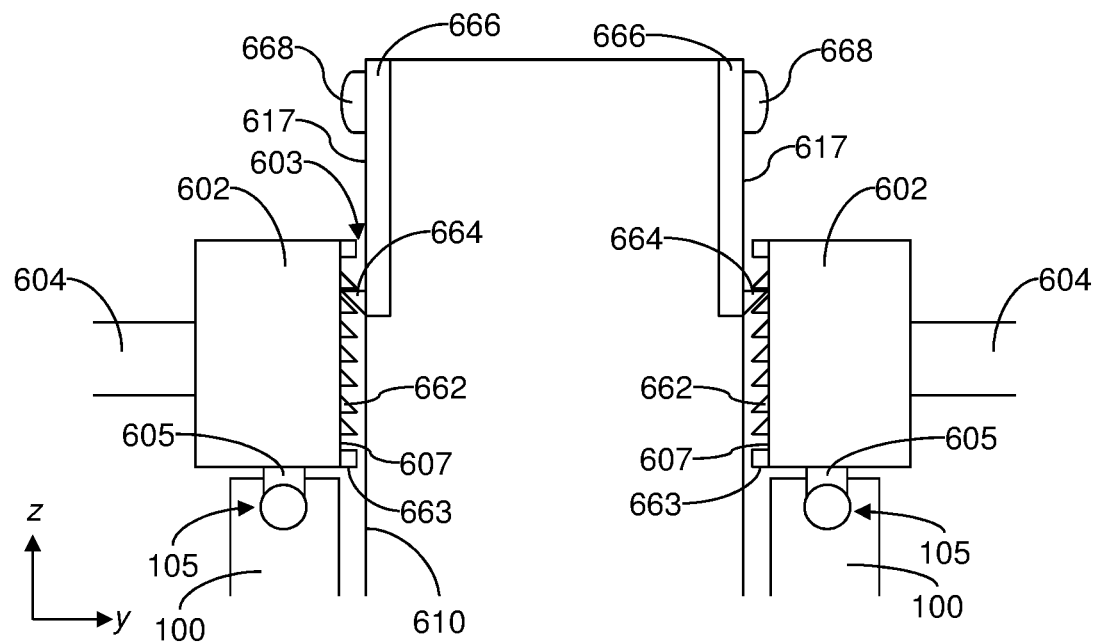
FIG. 5D illustrates an example coupling between a manipulator and the outer/inner blades for the example dissection system of FIG. 5A.

FIG. 5D illustrates an example configuration for coupling the manipulator 602 to the outer blade 610 and the inner blade 620. The example configuration allows the manipulator 602 to be operated so that the outer blade 610 and the inner blade 620 move axially along the z-axis to penetrate the cornea 2 without rotating about the z-axis.

As shown in FIG. 5D, the manipulator 602 is coupled to the housing 100. The manipulator 602 can rotate about the z-axis relative to the housing 100, but cannot move according to other degrees of freedom relative to the housing 100. For instance, the manipulator 602 may include engagement structures 605 that can snap into an annular track 105 running along a surface (e.g., top surface) of the housing 100; the engagement structures 605 can move within the annular track 105 to allow rotation of the manipulator 602.

The manipulator 602 includes a central passageway 603. The outer blade 610 is disposed within the central passageway 603. The outer blade 610 includes an outer surface 617 that faces an inner surface 607 of the manipulator 602 within the central passageway 603. The manipulator 602 includes a thread 662 that spirals along the inner surface 607. The outer blade 610 includes tabs 664 that are biased to extend radially outward from the outer surface 617 and engage the thread 662. When the manipulator 602 is rotated in a first direction about the z-axis, the thread 662 applies a force against the tabs 664 in the negative-z direction. This force causes the outer blade 610, as well as the inner blade 620 fixed to the outer blade 610, to move in the negative-z direction and penetrate the cornea 2. The movement of the outer blade 610 and the inner blade 620 does not involve rotation about the z-axis relative to the housing 100 and the cornea 2. In some cases, the housing 100 may include one or more guide structures to engage the outer blade 610 and prevent such rotation while allowing movement along the z-axis. Rotation of the manipulator 602 in the first direction stops when the outer blade 610 and the inner blade 620 reach their respective desired penetration depths $t_1$ and $t_1+t_2$, respectively.

Once the outer blade 610 and the inner blade 620 reach the desired penetration depths, the manipulator 602 can be further operated to make additional cuts (e.g., transverse cuts) to allow the anterior portion 2a and the posterior portion 2b to be removed. In particular, the manipulator 602 can be rotated in a second direction about the z-axis to cause the wires 651, 652 to rotate about the z-axis. This second direction is opposite from the first direction in which the manipulator 602 is rotated to move the outer blade 610 and the inner blade 620 in the negative-z direction. Rotation of the wires 651 makes an annular cut at the penetration depth $t_1$, between the outer cut to the inner cut. Meanwhile, rotation of the wire 652 makes a circular cut at the penetration depth of $t_1+t_2$.

As shown in FIG. 5D, when the manipulator 602 is rotated in the second direction about the z-axis, the outer blade 610 and the inner blade 620 do not move in the positive-z direction. Although the thread 662 may apply a force against the tabs 664 in the positive-z direction, the tabs 664 are shaped (e.g., with an angled surface) so that such force also pushes the tabs 664 radially inward. The force overcomes the radially outward bias of the tabs 664, causing the tabs to move radially inward. This inward movement of the tabs 664 prevents the force in the positive-z direction from pushing the outer blade 610 and the inner blade 620 in the positive-z direction.

The manipulator 602 includes tabs 663 that engage the tabs 664 of the outer blade 610 as the manipulator is rotated in the second direction. The engagement between the tabs 663, 664 causes the outer blade 610 as well as the inner blade 620 to rotate in the second direction with the manipulator 602. The wires 651, 652 rotate correspondingly with the outer blade 610 and inner blade 620. Because the thread 662 does not move the outer blade 610 and inner blade 620 along the z-axis, the wires 651, 652 rotate on the x-y planes at the depths $t_1$ and $t_1+t_2$, respectively, to produce the desired cuts.

Once the cuts with the wires 651, 652 are completed, the anterior portion 2a and the posterior portion 2b can be removed from the cornea 2. In some cases, withdrawal of the dissection system 40 from the cornea 2 also removes the dissected tissue.

The outer blade 610 and the inner blade 620 can be reset relative to the manipulator 602 and the housing 100 for a subsequent dissection procedure. As shown in FIG. 5D, each tab 664 is disposed on one end of a biasing structure 666 positioned within the outer blade 610. The biasing structure 666 pushes the tabs 664 radially outward through the outer surface 617 of the outer blade 610. A button 668 is disposed near the other end of the biasing structure 666 and also extends radially outward through the outer surface 617. When the button 668 is pushed radially inward, resulting movement of the biasing structure 666 causes the tab 664 to also move radially inward and to disengage the track 662 of the manipulator 602. Accordingly, the buttons 668 can be squeezed together with fingers to allow the outer blade 610, as well as the inner blade 620, to be moved in the positive-z direction, back to a starting position for the subsequent dissection procedure.

Figure 5E:
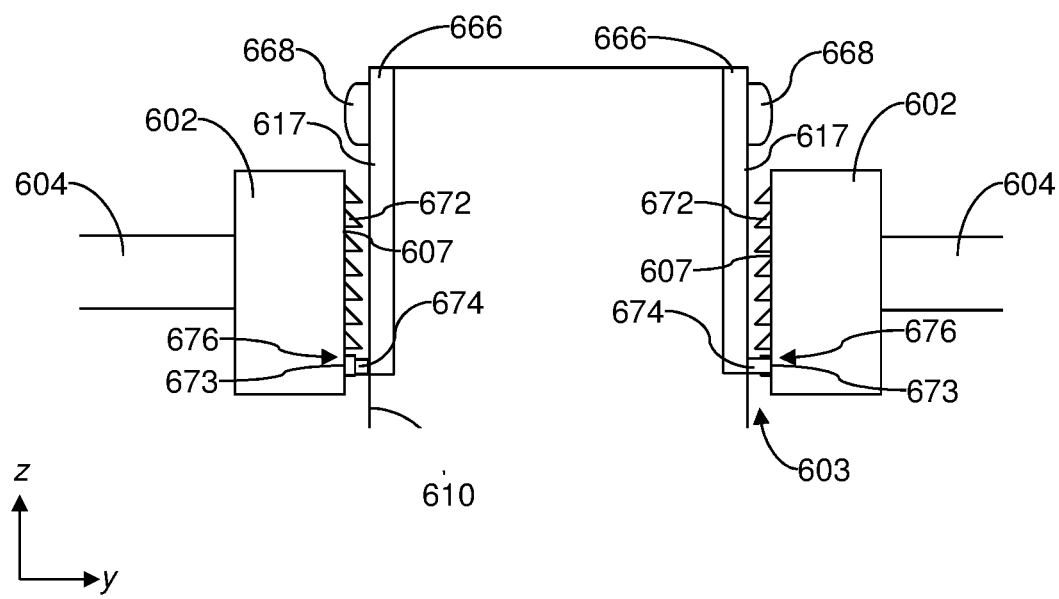
FIG. 5E illustrates another example coupling between a manipulator and the outer/inner blades for the example dissection system of FIG. 5A.

FIG. 5E illustrates an alternative configuration for coupling the manipulator 602 to the outer blade 610 and the inner blade 620. Similar to the configuration of FIG. 5D, the manipulator 602 is coupled to the housing 100 (not shown). The manipulator 602 can rotate about the z-axis relative to the housing 100, but cannot move according to other degrees of freedom relative to the housing 100. In addition, the manipulator 602 includes the central passageway 603. The outer blade 610 is disposed within the central passageway 603. The outer surface 617 of the outer blade 610 faces the inner surface 607 of the manipulator 602.

As shown in FIG. 5E, the manipulator 602 includes the thread 662 which spirals along the inner surface 607. The outer blade 610 includes tabs 674 that are biased to extend radially outward from the outer surface 617 and engage the threads 672. When the manipulator 602 is rotated in a first direction about the z-axis, the thread 672 applies a force against the tabs 674 in the negative-z direction. This force causes the outer blade 610, as well as the inner blade 620 fixed to the outer blade 610, to move in the negative-z direction and penetrate the cornea 2. The movement of the outer blade 610 and the inner blade 620 does not involve rotation about the z-axis relative to the housing 100 and the cornea 2. In some cases, the housing 100 may include one or more guide structures to engage the outer blade 610 and prevent such rotation while allowing movement along the z-axis.

Unlike the configuration of FIG. 5D, the tabs 674 continue to move along the thread 672 until they enter a groove 676 at the end of the thread 672. At this point, the outer blade 610 and the inner blade 620 have reached their desired penetration depths $t_1$ and $t_1+t_2$, respectively. With the tabs 674 positioned in the groove 676, the thread 672 can no longer apply a force to the tabs 674 and the manipulator 602 can be further rotated in the same first direction about the z-axis to make additional cuts to allow the anterior portion 2a and the posterior portion 2b to be removed.

The manipulator 602 includes tabs 673 that engage the tabs 664 of the outer blade 610 as the manipulator continues to rotate in the first direction. The engagement between the tabs 663, 664 causes the outer blade 610 as well as the inner blade 620 to rotate in the first direction with the manipulator 602. The wires 651, 652 rotate correspondingly with the outer blade 610 and inner blade 620. Because the thread 672 does not move the outer blade 610 and inner blade 620 along the z-axis, the wires 651, 652 rotate on the x-y planes at the depths $t_1$ and $t_1+t_2$, respectively, to produce the desired cuts. As described above, rotation of the wires 651 makes an annular cut at the penetration depth $t_1$, between the outer cut to the inner cut. Meanwhile, rotation of the wire 652 makes a circular cut at the penetration depth of $t_1+t_2$.

The outer blade 610 and the inner blade 620 can be reset relative to the manipulator 602 and the housing 100 for a subsequent dissection procedure. As shown in FIG. 5E, each tab 674 is disposed on one end of the biasing structure 666 positioned within the outer blade 610. The biasing structure 666 pushes the tabs 674 radially outward through the outer surface 617 of the outer blade 610. A button 668 is disposed near the other end of the biasing structure 666 and also extends radially outward through the outer surface 617. When the button 668 is pushed radially inward, resulting movement of the biasing structure 666 causes the tab 674 to also move radially inward and allows the tab 674 to disengage the track 672 of the manipulator 602. Accordingly, the buttons 668 can be squeezed together with fingers to allow the outer blade 610, as well as the inner blade 620, to be moved in the positive-z direction, back to a starting position for the subsequent dissection procedure.

Figure 6A:
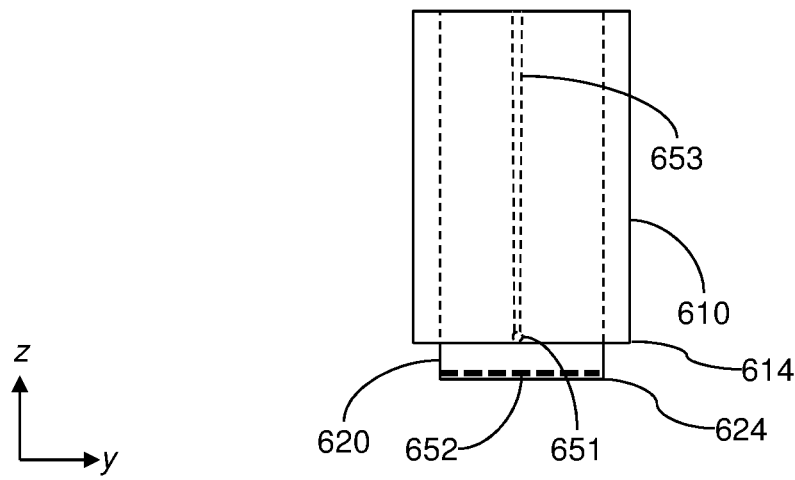
FIG. 6A illustrates aspects of an alternative cutting mechanism for making cuts after penetration of outer/inner blades into the cornea with a dissection system, according to aspects of the present disclosure.
Figure 6B:
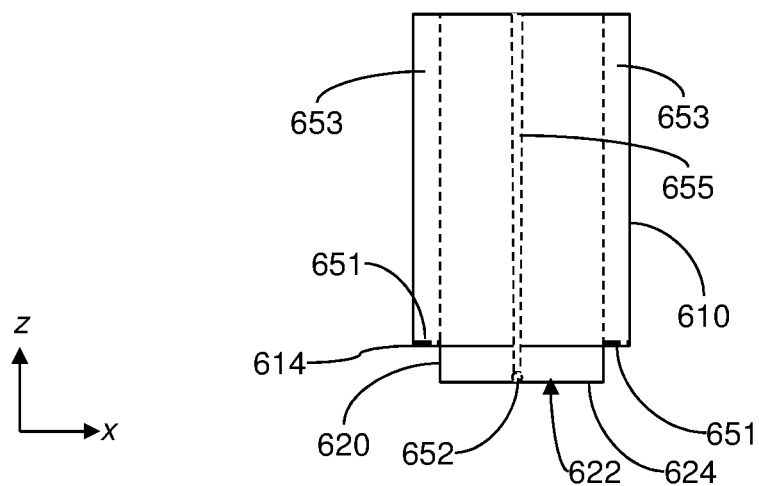
FIG. 6B illustrates further aspects of the alternative cutting mechanism of FIG. 6A.

As shown in FIGS. 5A-C, the wires 651, 652 in the example dissection system 40 have sufficient tension and sharpness to cut through the cornea 2 as the outer blade 610 and the inner blade 620 penetrate the cornea 2. Operation of the manipulator 602 to rotate the wires 651, 652 can also increase the tension in the wires 651, 652. Alternative embodiments, however, may provide additional support for the movement of the wires 651, 652 in the negative-z direction. For instance, FIGS. 6A-B illustrates the outer blade 610 and the inner blade 620, as well as the wires 651, 652 described above. FIG. 6A shows a support structure 653 extending between the outer blade 610 and the inner blade 620 and to the cutting edge 614 of the outer blade 610. One of the wires 651 is disposed at the end of the support structure 653 and aligned with the cutting edge 614. The end of the support structure 653 may be recessed or otherwise shaped to engage the wire 651 further. An additional support structure 653 (not shown) may be implemented with the other wire 651. Meanwhile, FIG. 6B shows a support structure 655 extending to the cutting edge 624 within the central passageway 622 of the inner blade 620. The wire 652 is disposed at the end of the support structure 655 and aligned with the cutting edge 624. The end of the support structure 655 may be recessed or otherwise shaped to engage the wire 652 further. The support structures 653, 655 move with the outer blade 610 and the inner blade 620 as they penetrate the cornea 2. Advantageously, the support structures 653, 655 help the wires 651, 652 to move through the cornea 2. When the outer blade 610 and the inner blade 620 reach their respective desired penetration depths, the manipulator 602 may be operated as described above to make the additional cuts with the wires 651, 652. In this case, the wires 651, 652 disengage from the respective support structures 653, 655 to rotate with the manipulator 602.

As shown in FIGS. 6A-B, the support structures 653, 655 may have a wedge-like or blade-like shapes extending substantially along the length of the outer blade 610 and the inner blade 620, respectively. In other embodiments, however, the support structures 653, 655 may have alternative shapes. For instance, the support structures 653, 655 may be shorter cross-bars that extend across and above the wires 653, 655 to provide support.

Figure 7A:
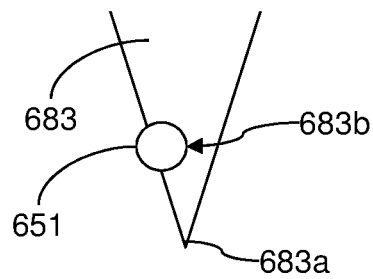
FIG. 7A illustrates aspects of an alternative cutting mechanism for making cuts after penetration of outer/inner blades into the cornea with a dissection system, according to aspects of the present disclosure.
Figure 7B:
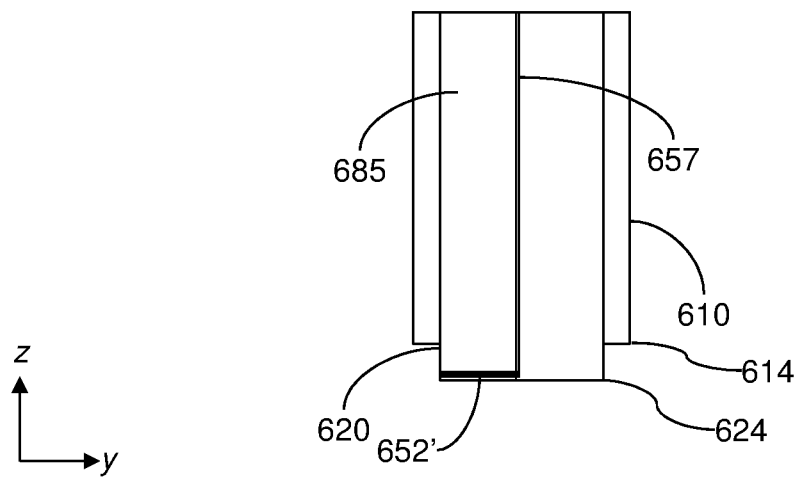
FIG. 7B illustrates a cross-sectional view of further aspects of the alternative cutting mechanism of FIG. 7A.
Figure 7C:
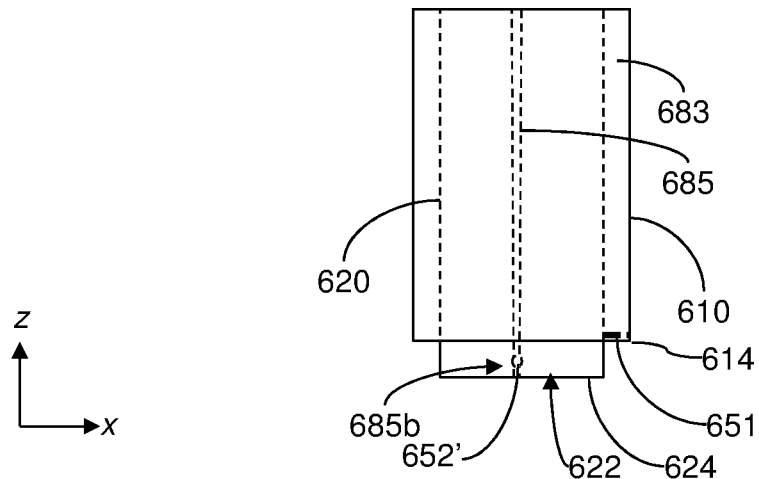
FIG. 7C illustrates yet further aspects of the alternative cutting mechanism of FIG. 7A.

FIGS. 7A-C illustrate an alternative approach for supporting for the movement of the wires in the negative-z direction. For instance, FIG. 7A illustrates a support structure 683 for a wire 651. (In contrast to the examples above, a single wire 651 is employed here.) The end 683a of the support structure 683 provides a leading edge as the outer blade 610 and the inner blade 620 penetrate the cornea 2. In FIG. 7A, the support structure 683 includes a recess 683b that receives the wire 651 above the end 683a of the support structure 683. In contrast, the wire 651 in FIGS. 6A-C is positioned below the support structure 653 and provides the leading edge. Advantageously, the end 683a may be sharper than the wire 651 and can cut through the cornea 2 more easily while the wire 251 remains in the recess 683b.

When the outer blade 610 and the inner blade 620 reach the respective desired penetration depths, the manipulator 602 may be operated to disengage the wire 651 from the recess 683b in the support structure 683 and to rotate the wire 651 about the z-axis to produce the cuts to help remove the anterior portion 2a. Although the wire 651 is received in the recess disposed above the end 683a of the support structure 683, the support structure 683 delivers the wire 651 to a depth where the wire 251 can provide an effective cut near the penetration depth $t_1$ (e.g., within approximately 5 µm).

To make the circular cut at or near the penetration depth $t_1+t_2$, a wire 652' as shown in the views of FIGS. 7B-C may be employed. The support structure 685 for the wire 652' may be configured to receive the wire 652' in a recess 685b in a manner similar to the support structure 683. In contrast to the support structure 655 and the wire 652 which extends across the entire diameter of the inner blade 620, the wire 652' extends across the radius of the inner blade 620. The wire 652' extends from a center support 657 to an inner wall of the inner blade 620. The wire 652' can rotate about the center support 657 to make the desired circular cut.

In FIGS. 7A-C, the rotation of the wires 651, 652' starts from one side of the support structures 683, 685 (i.e., out of the recesses 683b, 685b) and ends on the other side of the support structures 683, 685, respectively. As such, the wires 651, 652' are blocked by the support structures 683, 685 from making complete annular and circular cuts, respectively. The cuts by the wires 651, 652', however, are sufficient to allow removal of the anterior portion 2a and posterior portion 2b, respectively.

Although the inner and outer blades of the example embodiments above may have substantially circular profiles, it is understood that the other embodiments may employ other profiles to make cuts of different shapes, e.g., elliptical cuts. Additionally, it is understood that the blade assemblies in other embodiments may be configured to make non-concentric inner and outer cuts. Furthermore, it is understood that the blade assemblies in other embodiments may include more than two blades.

Although the inner cuts made by the inner blade in the example implementations above may have penetration depths that extend through the endothelium, it is understood that other implementations may employ penetration depths that do not extend completely to the endothelium. Furthermore, although the blade assemblies of the example embodiments above may remove a volume of corneal tissue having a mushroom shape, it is contemplated that blade assemblies in other embodiments may be configured to make cuts that allow corneal tissue to be removed according to other shapes.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

We claim:

1. A dissection system for corneal transplants, comprising:
   a housing including a contact side configured to be positioned against a cornea, the housing including an interior passageway with an opening at the contact side;
   a blade assembly disposed in the interior passageway of the housing, the blade assembly including a first blade and a second blade, the first blade including a first cutting edge, the second blade including a second cutting edge, the first blade and the second blade being movable relative to the housing such that the first cutting edge and the second cutting edge extend past the opening of the housing and out of the interior passageway, wherein the first cutting edge is configured to produce a first cut in the cornea disposed at the contact side and the second cutting edge is configured to produce a second cut in the cornea, the first cut and the second cut defining a volume of tissue for removal from the cornea; and
   one or more manipulators configured to move the first blade and the second blade relative to the housing,
   wherein the blade assembly includes a first blade depth controller configured to determine a first depth produced by the first cut into the cornea, and a second blade depth controller configured to determine a second depth produced by the second cut into the cornea,
   the first blade depth controller sets a position of one or more first stops to stop movement of the first cutting edge when the first cutting edge extends past the opening of the housing and out of the interior passageway by a first distance, and
   the second blade depth controller sets a position of the second cutting edge relative to the first cutting edge according to a second distance.

2. The dissection system of claim 1, wherein the first cutting edge and the second cutting edge are substantially circular, and the substantially circular first cutting edge is concentric with the substantially circular second cutting edge.

3. The dissection system of claim 1, wherein the first cutting edge and the second cutting edge are substantially circular, and the substantially circular first cutting edge has a first diameter that is larger than a second diameter of the second cutting edge.

4. The dissection system of claim 1, wherein the second cutting edge is configured to extend past the opening of the housing by a larger distance than the first cutting edge, the second cut extending to the second depth into the cornea that is larger than the first depth of the first cut into the cornea based on the larger distance.

5. The dissection system of claim 4, wherein the first cutting edge and the second cutting edge are substantially circular, and first cutting edge has a first diameter that is larger than a second diameter of the second cutting edge.

6. The dissection system of claim 1, wherein the volume of tissue includes: (i) an anterior portion defined by the first cut and extending from an epithelial surface of the cornea to a first depth in a stroma of the cornea, and (ii) a posterior portion defined by the second cut extending from the first depth to a second depth.

7. The dissection system of claim 6, wherein the first cut and the second cut are substantially circular, the first cut having a first diameter that is larger than a second diameter of the second cut, the anterior portion having a substantially circular profile with the first diameter, and the posterior portion having a substantially circular profile with the second diameter.

8. The dissection system of claim 1, wherein the second blade depth controller sets a position of one or more second stops to stop movement of the second cutting edge when the second cutting edge extends past the opening of the housing and out of the interior passageway by a second distance.

9. The dissection system of claim 1, wherein the first blade and the second blade are coupled together in movement relative to the housing, the blade assembly includes one or more fixed stops to stop movement of the first blade and the second blade when the first cutting edge and the second cutting edge extend past the opening of the housing and out of the interior passageway by a first fixed distance and a second fixed distance, respectively.

10. The dissection system of claim 1, wherein the first blade and the second blade are coupled together in movement relative to the housing, and the one or more manipulators includes a single manipulator configured to move both the first blade and the second blade.

11. The dissection system of claim 1, wherein the one or more manipulators include a first manipulator configured to move the first blade relative to the housing and a second manipulator configured to move the second blade relative to the housing.

12. The dissection system of claim 1, wherein the one or more manipulators are configured to move the first blade and the second blade via one or more threaded couplings between the blade assembly and the housing.

13. The dissection system of claim 1, further comprising a negative pressure source, wherein the housing includes one or more vacuum channels with one or more vacuum openings at the contact end, the one or more vacuum channels coupled to the negative pressure source, and the vacuum openings configured to apply suction from the negative pressure source to the cornea to fix the housing against the cornea.

14. A dissection system for corneal transplants, comprising:
a housing including a contact side configured to be positioned against a cornea, the housing including an interior passageway with an opening at the contact side;
a blade assembly disposed in the interior passageway of the housing, the blade assembly including a first blade and a second blade, the first blade including a first cutting edge, the second blade including a second cutting edge, the first blade and the second blade being movable relative to the housing such that the first cutting edge and the second cutting edge extend past the opening of the housing and out of the interior passageway, wherein the first cutting edge is configured to produce a first cut in the cornea disposed at the contact side and the second cutting edge is configured to produce a second cut in the cornea, the first cut and the second cut defining a volume of tissue for removal from the cornea;
one or more manipulators configured to move the first blade and the second blade relative to the housing, and
one or more cutting mechanisms configured to make further cuts transverse to at least one of the first cut or the second cut, wherein the one or more cutting mechanisms include one or more wires, and the one or more manipulators are further configured to move the wires to make the transverse cuts after the first blade and the second blade make the first cut and the second cut, respectively.

15. The dissection system of claim 14, wherein the one or more cutting mechanisms include one or more wires, and a first wire extends between the first cutting edge and the second cutting edge and a second wire extends from across the second cutting edge.

16. The dissection system of claim 14, wherein the one or more cutting mechanisms include one or more wires, and the dissection system further comprising one or more support structures configured to support the one or more wires to move through the cornea as the first cutting edge moves to produce the first cut in the cornea and the second cutting edge moves to produce the second cut in the cornea.

17. The dissection system of claim 14, wherein the first cutting edge and the second cutting edge are substantially circular, and the substantially circular first cutting edge is concentric with the substantially circular second cutting edge.

18. The dissection system of claim 14, wherein the first cutting edge and the second cutting edge are substantially circular, and the substantially circular first cutting edge has a first diameter that is larger than a second diameter of the second cutting edge.

19. The dissection system of claim 14, wherein the second cutting edge is configured to extend past the opening of the housing by a larger distance than the first cutting edge, the second cut extending to a second depth into the cornea that is larger than a first depth of the first cut into the cornea based on the larger distance.

20. The dissection system of claim 19, wherein the first cutting edge and the second cutting edge are substantially circular, and first cutting edge has a first diameter that is larger than a second diameter of the second cutting edge.

21. The dissection system of claim 14, wherein the volume of tissue includes: (i) an anterior portion defined by the first cut and extending from an epithelial surface of the cornea to a first depth in a stroma of the cornea, and (ii) a posterior portion defined by the second cut extending from the first depth to a second depth.

22. The dissection system of claim 21, wherein the first cut and the second cut are substantially circular, the first cut having a first diameter that is larger than a second diameter of the second cut, the anterior portion having a substantially circular profile with the first diameter, and the posterior portion having a substantially circular profile with the second diameter.

23. The dissection system of claim 14, wherein the first blade and the second blade are coupled together in movement relative to the housing, the blade assembly includes one or more fixed stops to stop movement of the first blade and the second blade when the first cutting edge and the second cutting edge extend past the opening of the housing and out of the interior passageway by a first fixed distance and a second fixed distance, respectively.

24. The dissection system of claim 14, wherein the first blade and the second blade are coupled together in movement relative to the housing, and the one or more manipulators includes a single manipulator configured to move both the first blade and the second blade.

25. The dissection system of claim 14, wherein the one or more manipulators include a first manipulator configured to move the first blade relative to the housing and a second manipulator configured to move the second blade relative to the housing.

26. The dissection system of claim 14, wherein the one or more manipulators are configured to move the first blade and the second blade via one or more threaded couplings between the blade assembly and the housing.

27. The dissection system of claim 14, further comprising a negative pressure source, wherein the housing includes one or more vacuum channels with one or more vacuum openings at the contact end, the one or more vacuum channels coupled to the negative pressure source, and the vacuum openings configured to apply suction from the negative pressure source to the cornea to fix the housing against the cornea.

* * * * *

UNITED STATES PATENT AND TRADEMARK OFFICE
CERTIFICATE OF CORRECTION

| | |
|---|---|
| PATENT NO. | : 10,898,383 B2 |
| APPLICATION NO. | : 16/054066 |
| DATED | : January 26, 2021 |
| INVENTOR(S) | : Barker et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

Signed and Sealed this
Thirty-first Day of January, 2023

*Katherine Kelly Vidal*

Katherine Kelly Vidal
*Director of the United States Patent and Trademark Office*